(12) United States Patent
Abel et al.

(10) Patent No.: US 11,986,672 B2
(45) Date of Patent: May 21, 2024

(54) RADIATION TREATMENT PLANNING FOR DELIVERING HIGH DOSE RATES TO SPOTS IN A TARGET

(71) Applicant: Varian Medical Systems, Inc., Palo Alto, CA (US)

(72) Inventors: Eric Abel, San Jose, CA (US); Alexander Katsis, San Mateo, CA (US)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 134 days.

(21) Appl. No.: 17/681,612

(22) Filed: Feb. 25, 2022

(65) Prior Publication Data
US 2022/0176159 A1    Jun. 9, 2022

Related U.S. Application Data

(62) Division of application No. 16/591,838, filed on Oct. 3, 2019, now Pat. No. 11,291,859.

(51) Int. Cl.
*A61N 5/10* (2006.01)

(52) U.S. Cl.
CPC .......... *A61N 5/1038* (2013.01); *A61N 5/103* (2013.01); *A61N 2005/1087* (2013.01); *A61N 2005/1089* (2013.01); *A61N 2005/109* (2013.01)

(58) Field of Classification Search
CPC ............................................ A61N 5/103–1047
See application file for complete search history.

(56) References Cited

U.S. PATENT DOCUMENTS 6,222,544 B1    4/2001  Tarr et al.
6,260,005 B1    7/2001  Yang et al.
(Continued)

FOREIGN PATENT DOCUMENTS

CN    104001270 A    8/2014
CN    106730407 A    5/2017
(Continued)

OTHER PUBLICATIONS

M. McManus et al., "The challenge of ionisation chamber dosimetry in ultra-short pulsed high dose-rate Very High Energy Electron beams," Sci Rep 10, 9089 (2020), published Jun. 3, 2020,; hllps://doi.org/10.1038/s41598-020-65819-y.
(Continued)

*Primary Examiner* — Thaddeus B Cox
(74) *Attorney, Agent, or Firm* — Harness, Dickey & Pierce, P.L.C.

(57) ABSTRACT

Information that describes a target inside a patient to be treated with radiation is accessed from computer system memory. An arrangement of spots inside the target is determined. Each the spots corresponds to a location inside the target where a respective beam of radiation is to be directed during radiation treatment of the patient. A dose rate for each of the beams is determined. The dose rate for each beam is a dose delivered in less than one second to a spot corresponding to that beam. For example, each beam can deliver at least four grays (GY) in less than one second, and may deliver as much as 20 Gy to 50 Gy or 100 Gy or more in less than one second. A radiation treatment plan, that includes the arrangement of the spots and the dose rate for each of the beams, is stored in computer system memory.

20 Claims, 8 Drawing Sheets

(56) References Cited

U.S. PATENT DOCUMENTS

| | | |
|---|---|---|
| 6,379,380 B1 | 4/2002 | Satz |
| 6,411,675 B1 | 6/2002 | Llacer |
| 6,504,899 B2 | 1/2003 | Pugachev et al. |
| 6,993,112 B2 | 1/2006 | Hesse |
| 7,268,358 B2 | 9/2007 | Ma et al. |
| 7,453,983 B2 | 11/2008 | Schildkraut et al. |
| 7,515,681 B2 | 4/2009 | Ebstein |
| 7,560,715 B2 | 7/2009 | Pedroni |
| 7,590,219 B2 | 9/2009 | Maurer, Jr. et al. |
| 7,616,735 B2 | 11/2009 | Maciunas et al. |
| 7,623,623 B2 | 11/2009 | Raanes et al. |
| 7,778,691 B2 | 8/2010 | Zhang et al. |
| 7,807,982 B2 | 10/2010 | Nishiuchi et al. |
| 7,831,289 B2 | 11/2010 | Riker et al. |
| 7,835,492 B1 | 11/2010 | Sahadevan |
| 8,401,148 B2 | 3/2013 | Lu et al. |
| 8,406,844 B2 | 3/2013 | Ruchala et al. |
| 8,559,596 B2 | 10/2013 | Thomson et al. |
| 8,600,003 B2 | 12/2013 | Zhou et al. |
| 8,613,694 B2 | 12/2013 | Walsh |
| 8,636,636 B2 | 1/2014 | Shukla et al. |
| 8,644,571 B1 | 2/2014 | Schulte et al. |
| 8,716,663 B2 | 5/2014 | Brusasco et al. |
| 8,847,179 B2 | 9/2014 | Fujitaka et al. |
| 8,948,341 B2 | 2/2015 | Beckman |
| 8,986,186 B2 | 3/2015 | Zhang et al. |
| 8,995,608 B2 | 3/2015 | Zhou et al. |
| 9,018,603 B2 | 4/2015 | Loo et al. |
| 9,033,859 B2 | 5/2015 | Fieres et al. |
| 9,149,656 B2 | 10/2015 | Tanabe |
| 9,155,908 B2 | 10/2015 | Meltsner et al. |
| 9,233,260 B2 | 1/2016 | Slatkin et al. |
| 9,283,406 B2 | 3/2016 | Prieels |
| 9,308,391 B2 | 4/2016 | Liu et al. |
| 9,333,374 B2 | 5/2016 | Iwata |
| 9,517,358 B2 | 12/2016 | Velthuis et al. |
| 9,545,444 B2 | 1/2017 | Strober et al. |
| 9,636,381 B2 | 5/2017 | Basile |
| 9,636,525 B1 | 5/2017 | Sahadevan |
| 9,649,298 B2 | 5/2017 | Djonov et al. |
| 9,656,098 B2 | 5/2017 | Goer |
| 9,694,204 B2 | 7/2017 | Hårdemark |
| 9,776,017 B2 | 10/2017 | Flynn et al. |
| 9,786,093 B2 | 10/2017 | Svensson |
| 9,795,806 B2 | 10/2017 | Matsuzaki et al. |
| 9,884,206 B2 | 2/2018 | Schulte et al. |
| 9,931,522 B2 | 4/2018 | Bharadwaj et al. |
| 9,962,562 B2 | 5/2018 | Fahrig et al. |
| 9,974,977 B2 | 5/2018 | Lachaine et al. |
| 9,987,502 B1 | 6/2018 | Gattiker et al. |
| 10,007,961 B2 | 6/2018 | Grudzinski et al. |
| 10,071,264 B2 | 9/2018 | Liger |
| 10,092,774 B1 | 10/2018 | Vanderstraten et al. |
| 10,183,179 B1 | 1/2019 | Smith et al. |
| 10,206,871 B2 | 2/2019 | Lin et al. |
| 10,232,193 B2 | 3/2019 | Iseki |
| 10,258,810 B2 | 4/2019 | Zwart et al. |
| 10,279,196 B2 | 5/2019 | West et al. |
| 10,307,614 B2 | 6/2019 | Schnarr |
| 10,315,047 B2 | 6/2019 | Glimelius et al. |
| 10,413,755 B1 | 9/2019 | Sahadevan |
| 10,525,285 B1 | 1/2020 | Friedman |
| 10,549,117 B2 | 2/2020 | Vanderstraten et al. |
| 10,603,514 B2 | 3/2020 | Grittani et al. |
| 10,609,806 B2 | 3/2020 | Roecken et al. |
| 10,661,100 B2 | 5/2020 | Shen |
| 10,702,716 B2 | 7/2020 | Heese |
| 2007/0287878 A1 | 12/2007 | Fantini et al. |
| 2010/0178245 A1 | 7/2010 | Arnsdorf et al. |
| 2011/0006224 A1 | 1/2011 | Maltz et al. |
| 2011/0091015 A1 | 4/2011 | Yu et al. |
| 2012/0157746 A1 | 6/2012 | Meltsner et al. |
| 2012/0171745 A1 | 7/2012 | Itoh |
| 2013/0131428 A1* | 5/2013 | Jiang .................. A61N 5/1031 600/1 |
| 2013/0231516 A1 | 9/2013 | Loo et al. |
| 2013/0281999 A1* | 10/2013 | Adler .................. A61N 5/1077 606/33 |
| 2014/0275706 A1 | 9/2014 | Dean et al. |
| 2015/0011817 A1 | 1/2015 | Feng |
| 2015/0202464 A1 | 7/2015 | Brand et al. |
| 2015/0306423 A1 | 10/2015 | Bharat et al. |
| 2016/0279444 A1 | 9/2016 | Schlosser |
| 2016/0310764 A1 | 10/2016 | Bharadwaj et al. |
| 2017/0165502 A1 | 6/2017 | Claereboudt et al. |
| 2017/0189721 A1 | 7/2017 | Sumanaweera et al. |
| 2017/0203129 A1 | 7/2017 | Dessy |
| 2017/0281973 A1 | 10/2017 | Allen et al. |
| 2018/0021594 A1 | 1/2018 | Papp et al. |
| 2018/0043183 A1 | 2/2018 | Sheng et al. |
| 2018/0056090 A1 | 3/2018 | Jordan et al. |
| 2018/0099154 A1 | 4/2018 | Prieels |
| 2018/0099155 A1 | 4/2018 | Prieels et al. |
| 2018/0099159 A1 | 4/2018 | Forton et al. |
| 2018/0154183 A1 | 6/2018 | Sahadevan |
| 2018/0197303 A1 | 7/2018 | Jordan et al. |
| 2018/0236268 A1 | 8/2018 | Zwart et al. |
| 2019/0022407 A1 | 1/2019 | Abel et al. |
| 2019/0022409 A1 | 1/2019 | Vanderstraten et al. |
| 2019/0022422 A1 | 1/2019 | Trail et al. |
| 2019/0054315 A1 | 2/2019 | Isola et al. |
| 2019/0070435 A1 | 3/2019 | Joe Anto et al. |
| 2019/0168027 A1 | 6/2019 | Smith et al. |
| 2019/0255361 A1 | 8/2019 | Mansfield |
| 2019/0299027 A1 | 10/2019 | Fujii et al. |
| 2019/0299029 A1 | 10/2019 | Inoue |
| 2019/0351259 A1 | 11/2019 | Lee et al. |
| 2020/0001118 A1 | 1/2020 | Snider, III et al. |
| 2020/0022248 A1 | 1/2020 | Yi et al. |
| 2020/0030633 A1 | 1/2020 | Van Heteren et al. |
| 2020/0035438 A1 | 1/2020 | Star-Lack et al. |
| 2020/0069818 A1 | 3/2020 | Jaskula-Ranga et al. |
| 2020/0164224 A1 | 5/2020 | Vanderstraten et al. |
| 2020/0178890 A1 | 6/2020 | Otto |
| 2020/0197730 A1 | 6/2020 | Safavi-Naeini et al. |
| 2020/0254279 A1 | 8/2020 | Ohishi |
| 2020/0269068 A1 | 8/2020 | Abel et al. |
| 2020/0276456 A1 | 9/2020 | Swerdloff |
| 2020/0282232 A1 | 9/2020 | Khuntia et al. |
| 2020/0282234 A1 | 9/2020 | Folkerts et al. |
| 2020/0298023 A1 | 9/2020 | Cooley, III et al. |
| 2021/0252307 A1* | 8/2021 | Kontaxis ............. A61N 5/1047 |

FOREIGN PATENT DOCUMENTS

| | | |
|---|---|---|
| CN | 107362464 A | 11/2017 |
| CN | 109966662 A | 7/2019 |
| CN | 111481840 A | 8/2020 |
| CN | 111481841 A | 8/2020 |
| EA | 010207 | 6/2008 |
| EP | 0979656 A2 | 2/2000 |
| EP | 3178522 | 6/2017 |
| EP | 3338858 A1 | 6/2018 |
| EP | 3384961 A1 | 10/2018 |
| EP | 3421087 A1 | 1/2019 |
| EP | 3453427 A1 | 3/2019 |
| EP | 3586920 A1 | 1/2020 |
| JP | 2617283 B2 | 6/1997 |
| JP | 2019097969 A | 6/2019 |
| WO | WO-2007017177 A1 | 2/2007 |
| WO | WO-2010018476 A2 | 2/2010 |
| WO | WO-2013081218 A2 | 6/2013 |
| WO | WO-2013133936 A1 | 9/2013 |
| WO | WO-2014139493 A1 | 9/2014 |
| WO | WO-2015038832 A1 | 3/2015 |
| WO | WO-2015102680 A2 | 7/2015 |
| WO | WO-2016122957 A1 | 8/2016 |
| WO | WO-2017156316 A1 | 9/2017 |
| WO | WO-2017174643 A1 | 10/2017 |
| WO | WO-2018137772 A1 | 8/2018 |
| WO | WO-2018152302 A1 | 8/2018 |
| WO | WO-2019097250 A1 | 5/2019 |
| WO | WO-2019103983 A1 | 5/2019 |
| WO | WO-2019164835 A1 | 8/2019 |

(56) References Cited

FOREIGN PATENT DOCUMENTS

| WO | WO-2019166702 A1 | 9/2019 |
|---|---|---|
| WO | WO-2019185378 A1 | 10/2019 |
| WO | WO-2019222436 A2 | 11/2019 |
| WO | WO-2020018904 A1 | 1/2020 |
| WO | WO-2020064832 A1 | 4/2020 |
| WO | WO-2020107121 A1 | 6/2020 |
| WO | WO-2020159360 A1 | 8/2020 |
| WO | WO-2020181118 | 9/2020 |
| WO | WO-2020185544 | 9/2020 |

OTHER PUBLICATIONS

Ibrahim Oraiqat et al., "An Ionizing Radiation Acoustic Imaging {iRAI} Technique for Real-Time Dosimetric Measurements for FLASH Radiotherapy," Medical Physics, vol. 47, Issue10, Oct. 2020, pp. 5090-5101, First published: Jun. 27, 2020,; hllps://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS51bHNIdmllci5jb20vY29udGVudC9hcnRpY2xIL3BpaS9zMDE2NzgxNDAxNjMwMTcyNA==.pdf.

Susanne Auer et al., "Survival of tumor cells after proton irradiation with ultra-high dose rates," Radiation Oncology 2011, 6:139, Published Oct. 18, 2011,; DOI: hllps://doi.org/10.1186/1748-717X-6-139.

Cynthia E. Keen, "Clinical linear accelerator delivers FLASH radiotherapy," Physics World, Apr. 23, 2019, IOP Publishing Lid,; https://physicsworld.com/a/clinical-linear-accelerator-delivers-flash-radiotherapy.

Fan et al., "Emission guided radiation therapy for lung and prostate cancers: A feasibility study on a digital patient," Med Phys. Nov. 2012; 39(11): 7140-7152. Published online Nov. 5, 2012. <https://www.ncbi.nlm.nih.gov/pmc/arlicles/PMC3505203/> doi: 10.1118/1.4761951.

Favaudon et al., "Ultrahigh dose-rate, "flash" irradiation minimizes the side-effects of radiotherapy," Cancer/ Radiotherapy, vol. 19, Issues 6---7 , Oct. 2015 , pp. 526-531, Available online Aug. 12, 2015, https://doi.org/10.1016/j.canrad.2015.04.006.

O. Zlobinskaya et al., "The Effects of Ultra-High Dose Rate Proton Irradiation on Growlh Delay in the Treatment of Human Tumor Xenografts in Nude Mice," Radiation Research, 181(2):177-183. Published Feb. 13, 2014,; DOI: http://dx.doi.org/10.1667/RR13464.1.

Bjorn Zackrisson, "Biological Effects Of High Energy Radiation And Ultra High Dose Rates," UMEA University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with; dlose rates above 100 Gy/s," Radiotherapy and Oncology, vol. 124, Issue 3, Sep. 2017, pp. 365-369,; Available online May 22, 2017,; doi: 10.1016/j.radonc.2017.05.003.

BW Loo et al., "Delivery of Ultra-Rapid Flash Radiation Therapy and Demonstration of Normal Tissue Sparing After Abdominal Irradiation of Mice," International Journal of Radiation Oncology, Biology, Physics,; vol. 98, Issue 2, p. E16, Supplement: S Meeting Abstract: P003, Published: Jun. 1, 2017,; DOI: hllps://doi.org/10.1016/j.ijrobp.2017.02.101.

Bhanu Prasad Venkatesulu et al., "Ultra high dose rate (35 Gy/sec) radiation does not spare the normal tissue in cardiac and splenic models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp. 13685.

Andrei Pugachev et al., "Pseudo beam's-eye-view as applied to beam orientation selection in intensity-modulated radiation therapy," Int. J. Radiation Oncology Biol. Phys., vol. 51, Issue 5, pp. 1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With; Inlensity-Modulaled Radiation Therapy or Passive Scattering Proton Therapy and Enables Individualized Radical Radiotherapy for Extensive Stage IIIB Non-Small-Cell Lung Cancer: A Virtual Clinical Study," Int. J_ RadiationOncology Biol. Phys., vol. 77, No. 2, pp. 357-366, 2010, Available online Aug. 5, 2009,; DOI: https://doi.ora/10.1016/i.iirobo.2009.04.028.

A.J. Lomax et al., "Intensity modulated proton therapy: A clinical example," Medical Physics, vol. 28, Issue 3, Mar. 2001, pp. 317-324, First published: Mar. 9, 2001, https://doi.org/10.1118/1.1350587.

Lamberto Widesott et al., "Intensity-Modulated Proton Therapy Versus Helical Tomolherapy in Nasopharynx; Cancer: Planning Comparison and NTCP Evaluation," Int. J_ Radiation Oncology Biol. Phys., vol. 72, No. 2, pp. 589-596, Oct. 1, 2008, Available online Sep. 13, 2008,; DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for early and advanced breast cancer: an overview," Radial Oncol. 2006; 1: 22. Published online Jul. 20, 2006,; doi: 10.1186/1748-717X-1-22.

RaySearch Laboratories, "Leading the way in cancer treatment, Annual Reporl 2013," RaySearch Laboratories (publ), Stockholm, Sweden, 94 pages, Apr. 2014, <https://www.raysearchlabs.com/siteassels/about-overview/media-cenler/wp-re-ev-n-pdfs/brochures/raysearch-ar-2013> eng.pdf.

Redrik Carlsson, "Utilizing Problem Structure in Optimization of Radiation Therapy," KTH Engineering Sciences, Doctoral Thesis, Stockholm, Sweden, Apr. 2008, Optimization and Systems Theory, Deparlmenl of Mathematics, Royal Institute ofTechnology, Stockholm, Sweden, ISSN 1401-2294, <https://www.raysearchlabs.com/globalassels/about-overview/media-cenler/wp-re-ev-n-pdfs/publicalions/lhesis-> fredrik light.pdf.

Chang-Ming Charlie Ma, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

alterego-admin, "Conventional Radiation Therapy May Not Protect Healthy Brain Cells,"; Intemational Neuropsychiatric Association—INA, Oct. 10, 2019, https://inawebsite.org/conventional-radiation-therapy-may-not-protect-healthy-brain-cells.

Aafke Christine Kraan, "Range verification methods in particle therapy: underlying physics and Monie Carlo modeling," Frontiers in Oncology, Jul. 7, 2015, vol. 5, Article 150, 27 pages, doi: 10.3389/fonc.2015.00150.

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10. 1088/0031-9155/60/8/R155.

SE McGowan et al., "Treatment planning optimisation in proton therapy," Br J Radiol, 2013, 86, 20120288, The British Institute of Radiology, 12 pages, DOI: 10.1259.bjr.20120288.

Steven Van De Water et al., "Towards FLASH proton therapy: the impact of treatment planning and machine characlerislics on achiev-

(56) References Cited

OTHER PUBLICATIONS able dose rates," ACTA Oncologica, Jun. 26, 2019, vol. 58, No. 10, pp. 1462-1469, Taylo & Francis Group, DOI: 10.1080/0284186X.2019.1627416.

J-Groen, "FLASH optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a; clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepled Version: hllps://boris.unibe.ch/92814/8/dose_rate_project_revised_submit.pdf; Published Version: 2016, Physics in medicine and biology, 61(8), pp. 3208-3221. Institute of Physics Publishing IOP,; published Mar. 29, 2016, https://boris.unibe.ch/92814.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, pp. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, pp. 437-444, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, pp. 429-438, DOI: 10.14338/IJPT-16-00017.1.

Wenbo Gu et al., "Integrated Beam Orientation and Scanning-Spot Optimization in Intensity Modulated Proton; Therapy for Brain and Unilateral Head and Neck Tumors," Med Phys. Author manuscript; available in PMC Apr. 1, 2019 https://www.ncbi.nlm.nih.gov/pmc/articles/PMC5904040/; Published in final edited form as: Med Phys. Apr. 2018; 45(4): 1338--1350. Published online Mar. 1, 2018.; doi: 10.1002/mo.12788 Acceoted manuscriot online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, hllps://doi.org/10.1078/0939-3889-00198.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by Real-Time Imaging and Gating and Reduces Equipment Size," PLoS ONE, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.

R. M. De Kruijff, "Flash radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.

Mevion Medical Systems, "Focus On The Future: Flash Therapy," Press Releases, Sep. 16, 2019<https://www.mevion.com/newsroom/press-releases/focus-future-flash-therapy>.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, <https://www.iomp.org/iomp-news2-flash-radiolherapy/>.

Abdullah Muhammad Zakaria et al., "Ultra-High Dose-Rate, Pulsed (FLASH) Radiotherapy with Carbon Ions: Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020,; doi: hllps://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle radiolherapy using clinical proton, helium-, carbon- and oxygen ion beams," Oncolarget, Aug. 30, 2016, vol. 7, No. 35, pp. 56676-56689, published online: Aug. 1, 2016,; doi: 10.18632/oncolargel.10996.

Aetna Inc., "Proton Beam, Neutron Beam, and Carbon Ion Radiotherapy," 2020, No. 0270, http://www.aetna.com/cpb/medical/dala/200_299/0270.hlml.

Nicholas W. Colangelo et al., "The Importance and Clinical Implications of FLASH Ultra-High Dose-Rate Sludie! for Proton and Heavy Ion Radiotherapy," Radial Res. Author manuscript; available in PMC Jan. 1, 2021. <https://www.ncbi.nlm.nih.gov/pmc/articles/PMC6949397/> Published in final edited form as: Radial Res. Jan. 2020; 193(1): 1--4. Published online Oct. 28, 2019. doi: 10.1667/RR15537.1.

Vincent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.

FlashRad: Ultra-high dose-rate FLASH radiotherapy to minimize the complications of radiotherapy, 2014, https://siric.curie.fr/sites/default/files/aloms/files/flashrad.pdf.

Tami Freeman, "FLASH radiotherapy: from preclinical promise to the first human treatment," Physics World, Aug. 6, 2019, IOP Publishing Lid,; https://physicsworld.com/a/llash-radiotherapy-from-preclinical-promise-to-the-first-human-treatmenl.

Intraop Medical, Inc., "IntraOp and Lausanne University Hospital Announce Collaboration in FLASH adiotherapy," Jun. 18, 2020,; https://intraop.com/news-events/lausanne-universily-flash-radiotherapy-collaboration.

M.-C. Vozenin et al., "Biological Benefits of Ultra-high Dose Rate FLASH Radiotherapy: Sleeping Beauty Awoken," Clin Oncol {R Coll Radiol). Author manuscript; available in PMC Nov. 12, 2019. <https://www.ncbi.nlm.nih.gov/pmc/articles/PMC6850216/> Published in final edited form as: Clin Oncol {R Coll Radiol). Jul. 2019; 31(7): 407--415. Published online Aor. 19, 2019 doi: 10.1016/i.clon.2019.04.001.

(56) References Cited

OTHER PUBLICATIONS

Efstathios Kamperis et al., "A FLASH back to radiotherapy's past and then fast forward to the future," J Cancer Prev Curr Res. 2019;10(6): 142-144. published Nov. 13, 2019, DOI: 10.15406/jcpcr.2019.10.00407.

P. Symonds et al., "FLASH Radiotherapy: The Next Technological Advance in Radiation Therapy?", Clinical; Oncology, vol. 31, Issue 7, pp. 405-406, Jul. 1, 2019, The Royal College of Radiologists, Published by Elsevier Lid., DOI: https://doi.org/10.1016/j.clon.2019.05.011.

Swati Girdhani et al., "Abstract LB-280: Flash: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. B-280, American Association for Cancer Research,; DOI: https://doi.org/10.1158/1538-7445.AM2019-LB-280.

Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine doi: 10.1002/mp.13858. Epub Oct. 23, 2019. PMID: 31600830.

Manuela Buonanno et al., "Biological effects in normal cells exposed to FLASH dose rate protons," Radiother Oncol. Author manuscript; available in PMC Oct. 1, 2020. <https://www.ncbi.nlm.nih.gov/pmc/articles/PMC6728238/> Published in final edited form as: Radiother Oncol. Oct. 2019; 139: 51-55. Published online Mar. 5, 2019. doi: 10.1016/i.radonc.2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement, S164-S165, Sep. 1, 2019, Mini Oral Sessions, DOI: https://doi.org/10.1016/j.ijrobp.2019.06.187.

Inserm Press Office, "Radiotherapy 'flashes' to reduce side effects," Press Release, Jul. 16, 2014, https://presse.inserm.fr/en/radiotherapy-flashes-to-reduce-side-effects/13394.

Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-ratiaion-biology.

Maging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton--offer-next-generation-beam-delivery-advanced- <http://www.itnonline.com/content/pronova-and-medphoton--offer-next-generation-beam-delivery-advanced-> imaging-proton-therapy.

Oncolink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is-right-for-me.

Marco Durante et al., "Faster and safer? FLASH ultra-high dose rate in radiotherapy," Br J Radiol 2018; 91(1082): Jun. 28, 2017, British Institute of Radiology, Published Online: Dec. 15, 2017, https://doi.org/10.1259/bjr-20170628.

John R. Fischer, "PMB launches FLASH radiotherapy system for use in clinical trials," HealthCare Business News,Jun. 29, 2020, DOTmed.com, Inc., nttp://www.dotmed.com/news/story/51662 <http://www.dotmed.com/news/story/51662.

Marie-Catherine Vozenin et al., "The advantage of FLASH radiotherapy confirmed in mini-pig and cat-cancer patients," Clinical Cancer Research, Author Manuscript Published OnlineFirst Jun. 6, 2018, https://clincancerres.aacrjournals.org/content/clincanres/early/2018/06/06/1078-0432 .CCR-17-3375full.pdf.

\* cited by examiner

RADIATION TREATMENT PLANNING FOR DELIVERING HIGH DOSE RATES TO SPOTS IN A TARGET

RELATED U.S. APPLICATIONS

This application is a continuation (divisional) of the application with Ser. No. 16/591,838, entitled "Radiation Treatment Planning for Delivering High Dose Rates to Spots in a Target," by E Abel et al., filed Oct. 3, 2019, now U.S. Pat. No. 11,291,859 and hereby incorporated by reference in its entirety. This application is related to the application with Ser. No. 17/681,565, entitled "Radiation Treatment Planning for Delivering High Dose Rates to Spots in a Target," by E Abel et al., filed Feb. 25, 2022.

BACKGROUND

The use of radiation therapy to treat cancer is well known. Typically, radiation therapy involves directing a beam of high energy proton, photon, ion, or electron radiation ("therapeutic radiation") into a target, or target volume (e.g., a volume that includes a tumor or lesion).

Before a patient is treated with radiation, a treatment plan specific to that patient is developed. The plan defines various aspects of the therapy using simulations and optimizations based on past experiences. In general, the purpose of the treatment plan is to deliver sufficient radiation to the unhealthy tissue while minimizing exposure of surrounding healthy tissue to the radiation.

The planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome.

A relatively recent radiobiology study has demonstrated the effectiveness of delivering an entire, relatively high therapeutic radiation dose to a target within a single, short period of time. For example, each beam can deliver at least four grays (Gy) in less than one second, and may deliver as much as 20 Gy to 50 Gy or as much as 100 Gy or more in less than one second. This type of treatment is referred to generally herein as FLASH radiation therapy (FLASH RT).

Evidence to date suggests that FLASH RT advantageously spares normal, healthy tissue from damage when that tissue is exposed to a high radiation dose for only a very short period of time. FLASH RT thus introduces important constraints that are not considered in or achieved with conventional radiation treatment planning.

SUMMARY

Embodiments according to the present invention provide an improved method of radiation treatment planning, and improved radiation treatment based on such planning, for FLASH radiation therapy (FLASH RT).

In embodiments, information that describes a target inside a patient to be treated with radiation is accessed from computer system memory. An arrangement of spots inside the target is determined. Each of the spots corresponds to a location inside the target where a respective beam of radiation is to be directed during radiation treatment of the patient. A dose rate for each of the beams is determined. The dose rate for each beam is a dose delivered in less than one second to a spot corresponding to that beam. For example, each beam can deliver at least four Grays (GY) in less than one second, and may deliver as much as 20 Gy to 50 Gy or 100 Gy or more in less than one second. A radiation treatment plan, that includes the arrangement of the spots and the dose rate for each of the beams, is stored in computer system memory.

Embodiments according to the invention improve radiation treatment planning and the treatment itself by expanding FLASH RT to a wider variety of treatment modalities and combinations of treatment modalities (e.g., spatially fractionated grid radiation therapy, in addition to intensity modulated radiation therapy such as intensity modulated particle therapy). Treatment plans generated as described herein are superior for sparing normal tissue from radiation in comparison to conventional techniques by reducing, if not minimizing, the magnitude (and the integral in some cases) of the dose to normal tissue (outside the target) by design. Combining the normal tissue sparing of FLASH RT with the tumor-killing effectiveness of spatially fractionated grid radiation therapy enables escalation of radiation dose in most tumors without the associated toxicities of conventional RT, and increase the number of indications treatable with FLASH dose rates. Treatment planning, while still a complex task of finding a balance between competing and related parameters, is simplified relative to conventional planning.

In summary, embodiments according to this disclosure pertain to generating and implementing a treatment plan that is the most effective (relative to other plans) and with the least (or most acceptable) side effects (e.g., a lower dose rate outside of the region being treated). Thus, embodiments according to the invention improve the field of radiation treatment planning specifically and the field of radiation therapy in general. Embodiments according to the invention allow more effective treatment plans to be generated quickly. Also, embodiments according to the invention help improve the functioning of computers because, for example, by reducing the complexity of generating treatment plans, fewer computational resources are needed and consumed, meaning also that computer resources are freed up to perform other tasks.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Figure 1:
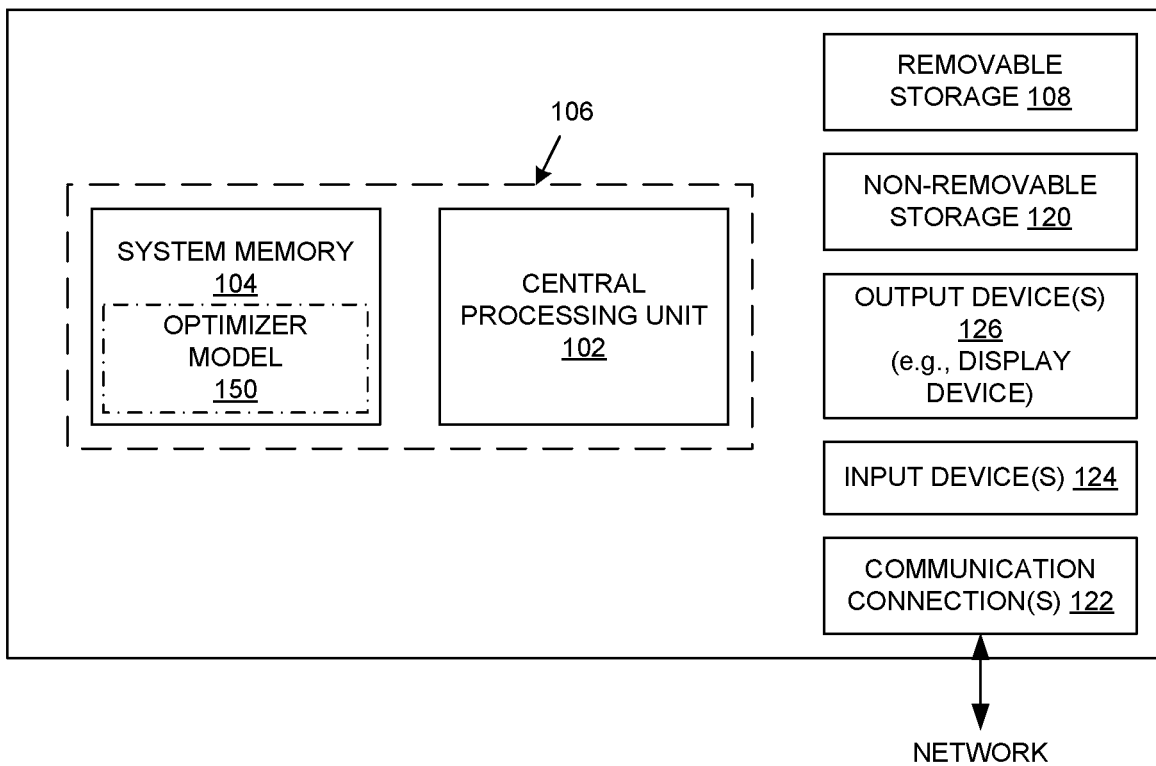
FIG. 1 is a block diagram of an example of a computer system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "generating," "representing," "applying," "indicating," "storing," "using," "adjusting," "including," "computing," or the like, refer to actions and processes (e.g., the flowcharts of FIGS. 7-10) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices. Terms such as "dose," "dose rate," or some other parameter or attribute generally refer to a dose value, dose rate value, attribute value, or parameter value, respectively; the use of such terms will be clear from the context of the surrounding discussion.

Portions of the detailed description that follows are presented and discussed in terms of methods. Although steps and sequencing thereof are disclosed in figures herein (e.g., FIGS. 7-10) describing the operations of those methods, such steps and sequencing are examples only. Embodiments are well suited to performing various other steps or variations of the steps recited in the flowcharts of the figures herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computer system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like associated with an "optimizer model" 150. However, the optimizer model 150 may instead reside in any one of the computer storage media used by the system 100, or may be distributed over some combination of the computer storage media, or may be distributed over some combination of networked computers. The functionality of the optimizer model 150 is described below.

Figure 2:
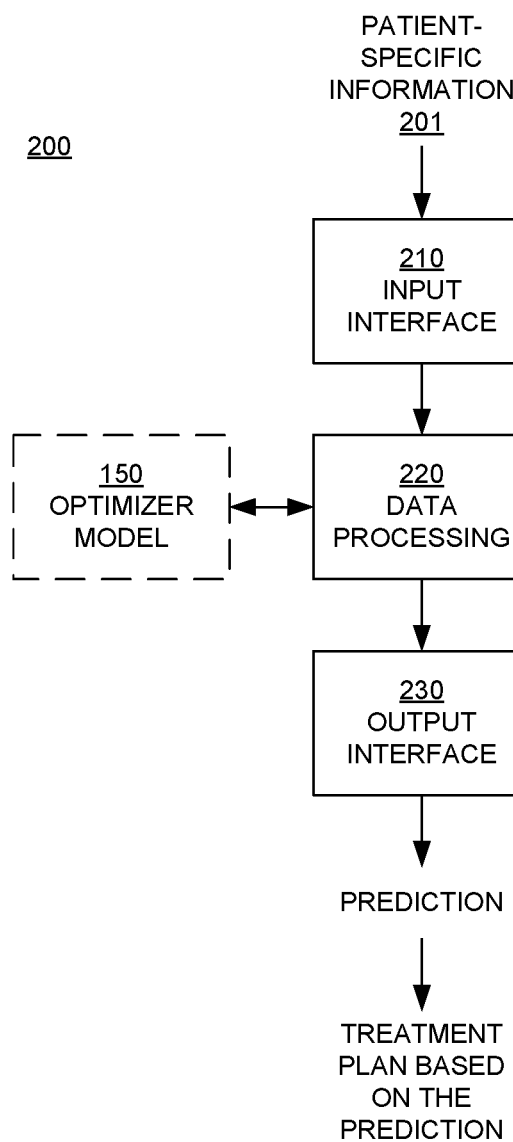
FIG. 2 is a block diagram illustrating an example of an automated radiation therapy treatment planning system in embodiments according to the present invention.

FIG. 2 is a block diagram illustrating an example of an automated radiation therapy treatment planning system 200 in embodiments according to the present invention. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computer system 100 (FIG. 1).

In the example of FIG. 2, the patient-specific information is provided to and processed by the optimizer model 150. The optimizer model 150 yields a prediction result. A treatment plan based on the prediction result can then be generated.

Figure 3:
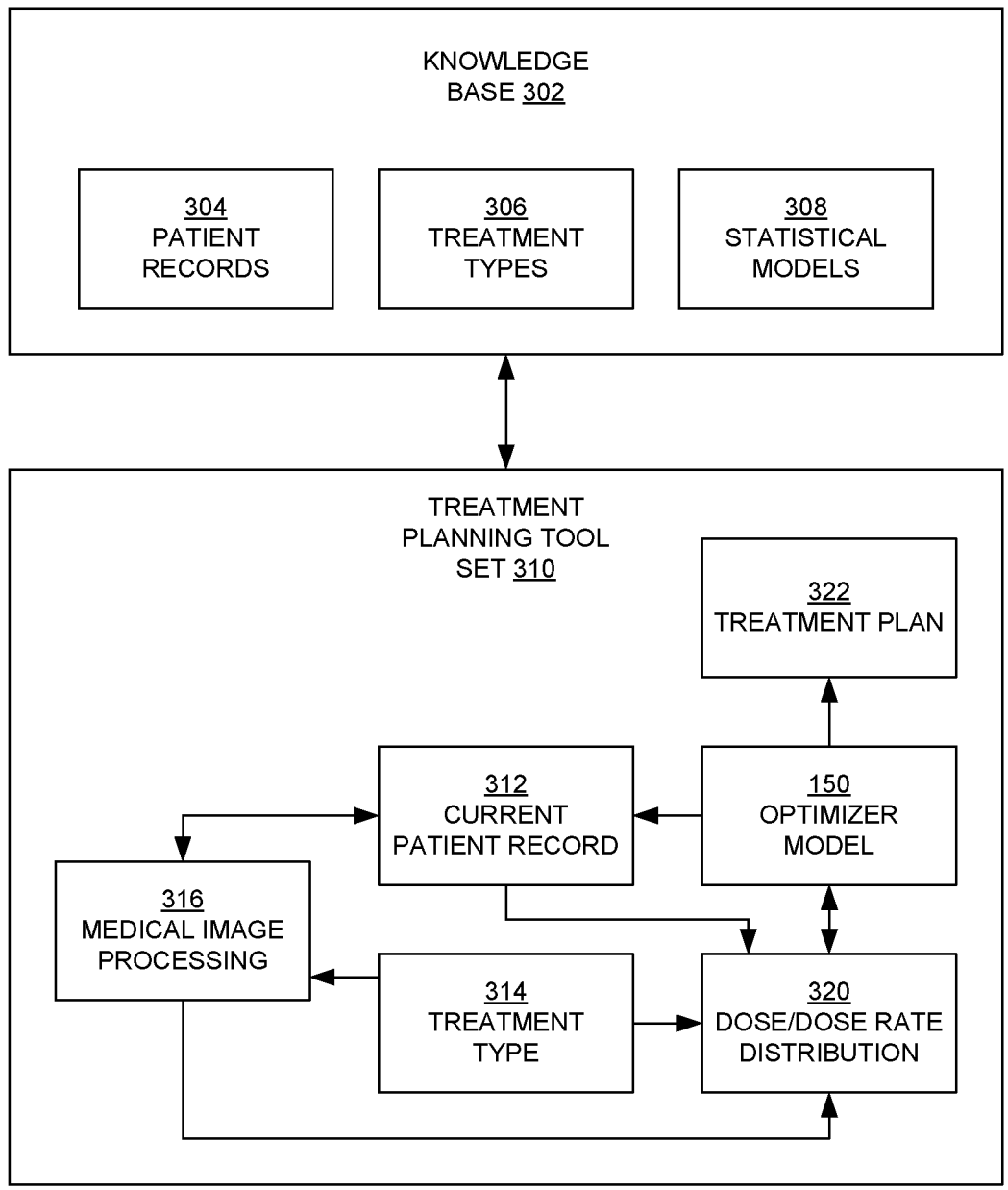
FIG. 3 illustrates a knowledge-based planning system in embodiments according to the present invention.

FIG. 3 illustrates a knowledge-based planning system 300 in embodiments according to the present invention. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, the optimizer model (module) 150, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. Patient outcomes, which can include normal tissue complication probability as a function of dose rate and patient-specific treatment-type outcomes can be included in the treatment planning process. The medical image processing module 316 provides automatic contouring and automatic segmentation of two-dimensional cross-sectional slides (e.g., from any imaging modality such as, but not limited to, computed tomography (CT), positron emission tomography-CT, magnetic resonance imaging, and ultrasound) to form a three-dimensional (3D) image using the medical images in the current patient record 312. Dose distribution maps and dose rate distribution maps are calculated by the dose and dose rate distribution module 320, which may utilize the optimizer model 150.

In embodiments according to the present invention, the optimizer model 150 uses a dose prediction model to provide, for example, a 3D dose distribution, fluences, and dose rates, and associated dose-volume histograms, dose rate-volume histograms, and irradiation time-volume histograms.

Figure 4A:
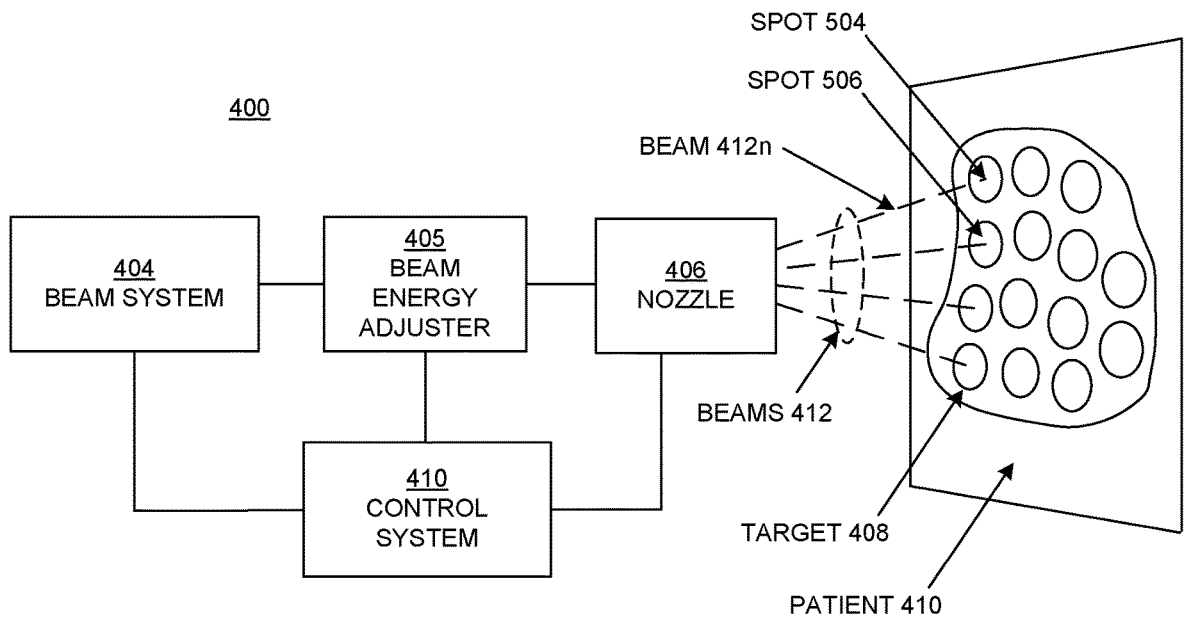
FIG. 4A is a block diagram showing selected components of a radiation treatment system upon which embodiments according to the present invention can be implemented.

FIG. 4A is a block diagram showing selected components of a radiation treatment system 400 upon which embodiments according to the present invention can be implemented. In the example of FIG. 4A, the radiation treatment system 400 includes a beam system 404 and a nozzle 406.

The beam system 404 generates and transports a beam. The beam can be a proton beam, electron beam, photon beam, ion beam, or atom nuclei beam (e.g., carbon, helium, and lithium). In embodiments, depending on the type of beam, the beam system 404 includes components that direct (e.g., bend, steer, or guide) the beam in a direction toward and into the nozzle 406.

In intensity modulated radiation therapy (IMRT) such as intensity modulated particle therapy (IMPT), the intensity of the beam is varied across each treatment region (target) in a patient. In embodiments, the radiation treatment system 400 also includes a beam energy adjuster 405 that can be used to adjust (e.g., reduce or modulate) the energy of the beam entering the nozzle 406. In an embodiment, the beam energy adjuster 405 is part of the nozzle 406. The term "beam energy adjuster" is used herein as a general term for a component or components that affect the energy of the beam, in order to control the range of the beam (e.g., the extent that the beam penetrates into a target), to control the dose delivered by the beam, and/or to control the depth dose curve of the beam, depending on the type of beam. For example, for a proton beam or an ion beam that has a Bragg peak, the beam energy adjuster 405 can control the location of the Bragg peak in a target volume 408 within a patient 410 supported on a patient support device (e.g., a chair or table) in a treatment room (see the discussion of FIG. 6 below). In various embodiments, the beam energy adjuster 405 includes a range modulator, a range shifter, or both a range modulator and a range shifter.

The target volume 408 may be an organ, a portion of an organ (e.g., a volume or region within the organ), a tumor, diseased tissue, or a patient outline. A target volume may include both unhealthy tissue (e.g., a tumor) and healthy tissue.

The control system 410 of FIG. 4A receives and implements a prescribed radiation treatment plan. In embodiments, the control system 410 includes a computer system having a processor, memory, an input device (e.g., a keyboard), and perhaps a display device, in well-known fashion. The control system 410 can receive data regarding operation of the radiation treatment system 400. The control system 410 can control parameters of the beam system 404, nozzle 406, and patient support device (not shown), including parameters such as the energy, intensity, direction, size, and/or shape of a beam, according to data it receives and according to the prescribed radiation treatment plan.

In the FIG. 4A embodiments, the nozzle 406 is used to aim the beams 412 toward various locations (e.g., the spots 504 and 506) in the target volume 408 according to the prescribed radiation treatment plan and under control of the control system 410. In embodiments, the nozzle 406 includes scanning magnets (not shown) that can be used to control the directions of the beams 412. As will be described, the beams 412 can be directed sequentially into the spots (e.g., a beam is directed into the spot 504, then another beam is directed into the spot 506, and so on).

Figure 4B:
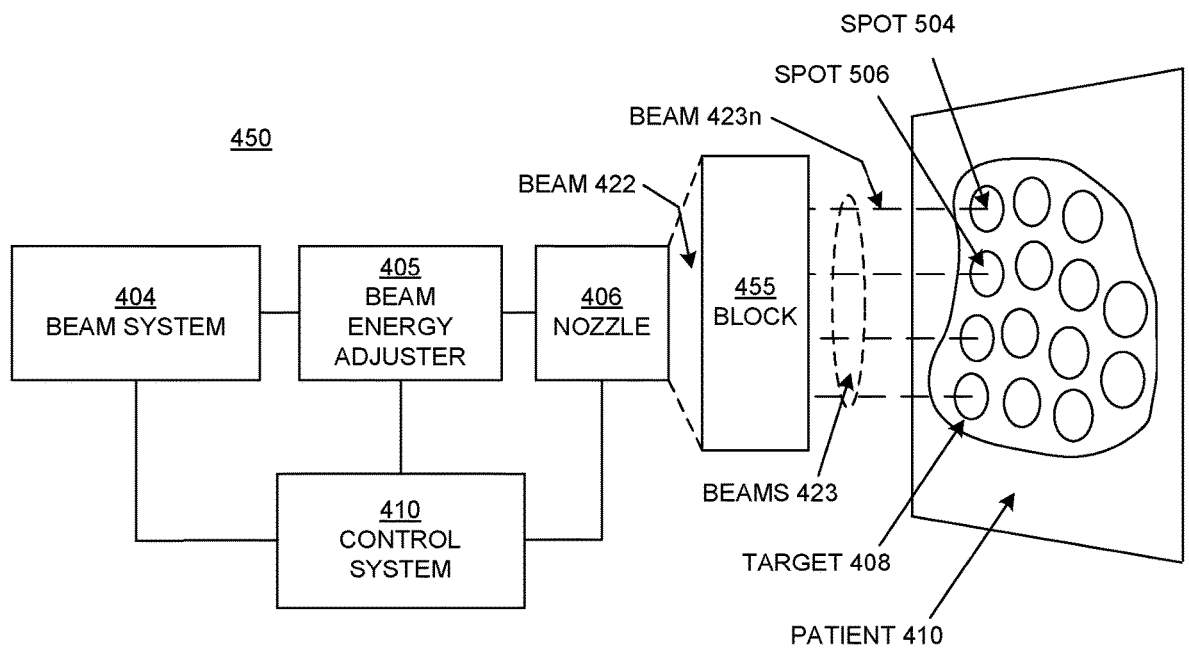
FIG. 4B is a block diagram showing selected components of a radiation treatment system upon which embodiments according to the present invention can be implemented.

FIG. 4B is a block diagram showing selected components of a radiation treatment system 450 upon which embodiments according to the present invention can be implemented. In contrast to the example of FIG. 4A, the radiation treatment system 450 includes a spatially fractionating radiotherapy block 455 between the system 450 and the target volume 408. The spatially fractionating radiotherapy block 455 can be, for example, a grid block or a multileaf collimator (MLC), and may be either a part of the nozzle 406 or a separate component positioned between the nozzle and the target volume 408.

Figure 4C:
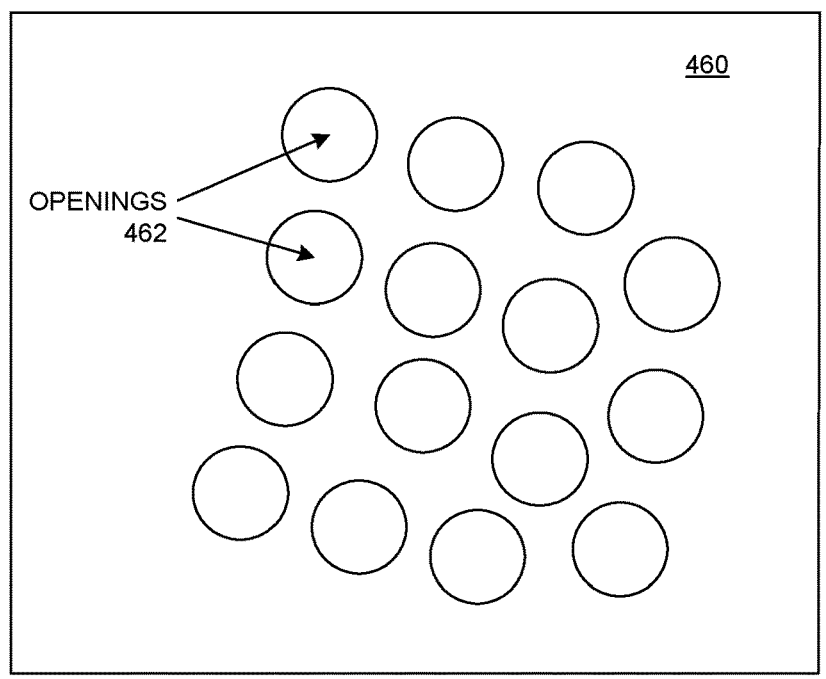
FIG. 4C illustrates a spatially fractionating radiotherapy block that can be used in embodiments according to the present invention can be implemented.

A beam's eye view of an example of a grid block 460 is shown in FIG. 4C. Generally speaking, portions of the beam 422 (the beams 423 of FIG. 4B) pass through openings 462 in the grid block 460, while the remaining portions of the beam 422 are blocked or attenuated by the grid block. The openings 462 in the grid block 460 are located so that they can be aligned with, or can align the beams 423 with, the spots (e.g., the spots 504 and 506) in the target volume 408. In a similar manner, leaves of an MLC (not shown) can be positioned so that they block portions of the beam and align unblocked portions of the beam 422 with the locations of the spots in the target volume 408.

Figure 5:
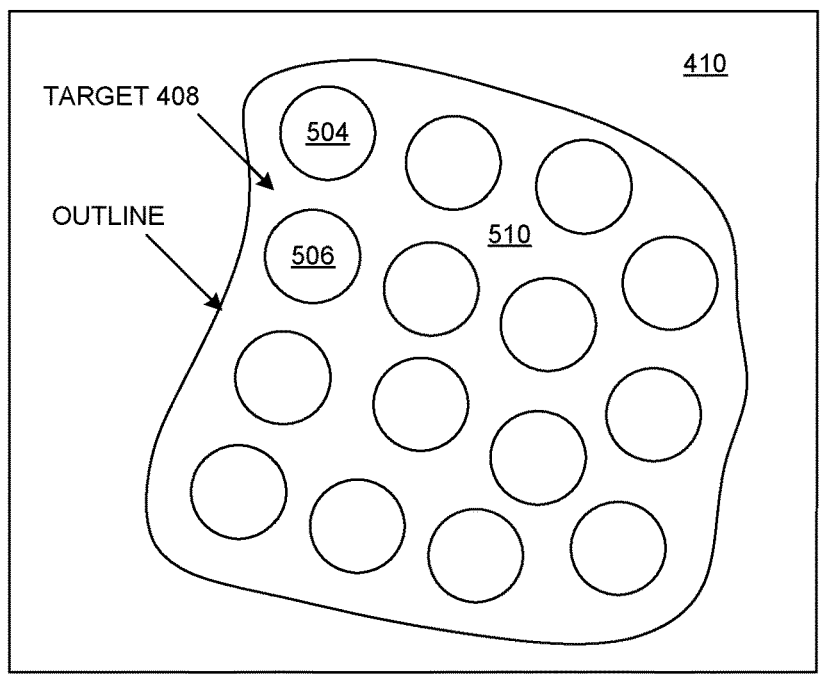
FIG. 5 illustrates an example of a beam's eye view of a target volume in embodiments according to the invention.

FIG. 5 illustrates an example of a beam's eye view of a target volume 408 in embodiments according to the invention. The target volume 408 can coincide with the shape of the object being treated (e.g., the outline of the target volume can coincide with the outline of a tumor), the target volume may be larger than the object being treated, or the target volume may correspond to a portion (a sub-volume) of the object being treated.

In embodiments according to the invention, the target volume 408 includes an arrangement of spots (e.g., the spots 504 and 506). With reference to FIG. 4A, the nozzle 406 is configured to emit a beam 412n (one of the beams 412) as a pencil beam, also referred to as a spot scanning beam. The target volume 408 may be irradiated with a raster scan (two-dimensional emission) of the pencil beams. Generally speaking, a first pencil beam is aimed at the first spot 504 in the target volume 408, a dose rate is delivered to that spot, then a second pencil beam is aimed at the second spot 506 in the target volume, a dose rate is delivered to the second spot, and so on. Thus, in embodiments implemented using the radiation treatment system 400, the beams 412 are delivered sequentially. More specifically, a beam is delivered to the first spot in the target volume (turned on) and then turned off, then a beam is delivered to the second spot in the target volume (turned on) and then turned off, and so on. Because the beams 412 are delivered sequentially, a different dose and dose rate can be delivered to each spot if so desired. This type of delivery and treatment may be referred to as spatially fractionated grid radiation therapy (SFGRT).

Each beam 412n may be turned on for only a fraction of a second. In embodiments according to the invention, each beam 412n delivers a relatively high dose rate (a relatively high dose in a relatively short period of time) to the target in that fraction of a second. For example, each beam 412n can deliver at least four (4) grays (Gy) in less than one second, and may deliver as much as 20 Gy to 50 Gy or 100 Gy or more in less than one second.

With reference to FIG. 4B, the nozzle 406 is configured to emit the beam 422 toward and into the spatially fractionating radiotherapy block 455. A dose rate is delivered to the spots (e.g., the spots 504 and 506) in the target volume 408 by the portions of the beam 422 (the beams 423) that are not blocked by the spatially fractionating radiotherapy block 450. Thus, in embodiments implemented using the radiation treatment system 450, the beams 423 can be delivered at the same time. Although the beams 423 are delivered at the same time, the spatially fractionating radiotherapy block 455 can be configured so that a different dose and dose rate can be delivered to each spot if so desired. As in the embodiments above, each beam 423n of the beams 423 delivers a relatively high dose rate (a relatively high dose in a relatively short period of time) to the target in at fraction of a second. For example, each beam 423n can deliver at least 4 Gy in less than one second, and may deliver as much as 20 Gy to 50 Gy or 100 Gy or more in less than one second. This type of delivery and treatment also may be referred to as SFGRT.

Figure 6:
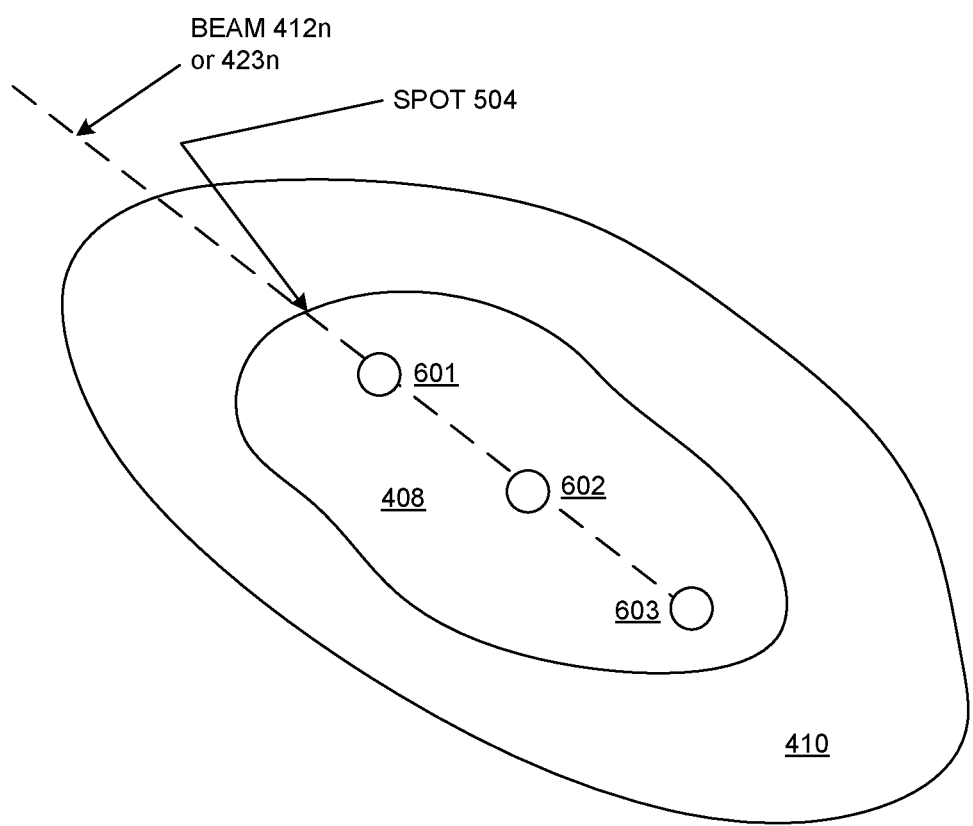
FIG. 6 illustrates a cross-sectional view of a target volume in embodiments according to the invention.

FIG. 6 illustrates a cross-sectional view of the target volume 408 in embodiments according to the invention. In the example of FIG. 6, the beam 412n/423n is directed at and through the spot 504 and into the target volume 408. The intensity of the beam 412n/423n can be varied using the beam energy adjuster 405, to control the range of the beam (e.g., the extent that the beam penetrates into a target), to control the dose delivered by the beam, and/or to control the depth dose curve of the beam, depending on the type of beam. For example, for a proton beam or an ion beam that has a Bragg peak, the beam energy adjuster 405 can control the location of the Bragg peak so that the Bragg peak is located at the point 603, then at the point 602, and then at the point 601 (or vice versa).

Figure 7:
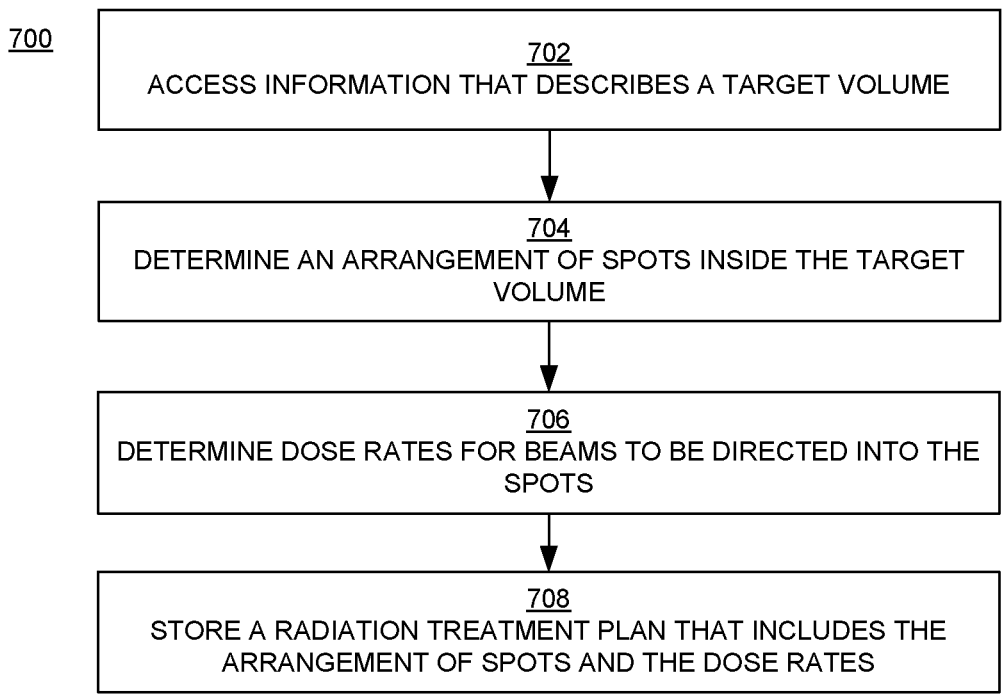
FIGS. 7, 8, and 9 are flowcharts of examples of computer-implemented operations for radiation treatment planning in embodiments according to the present invention.
Figure 8:
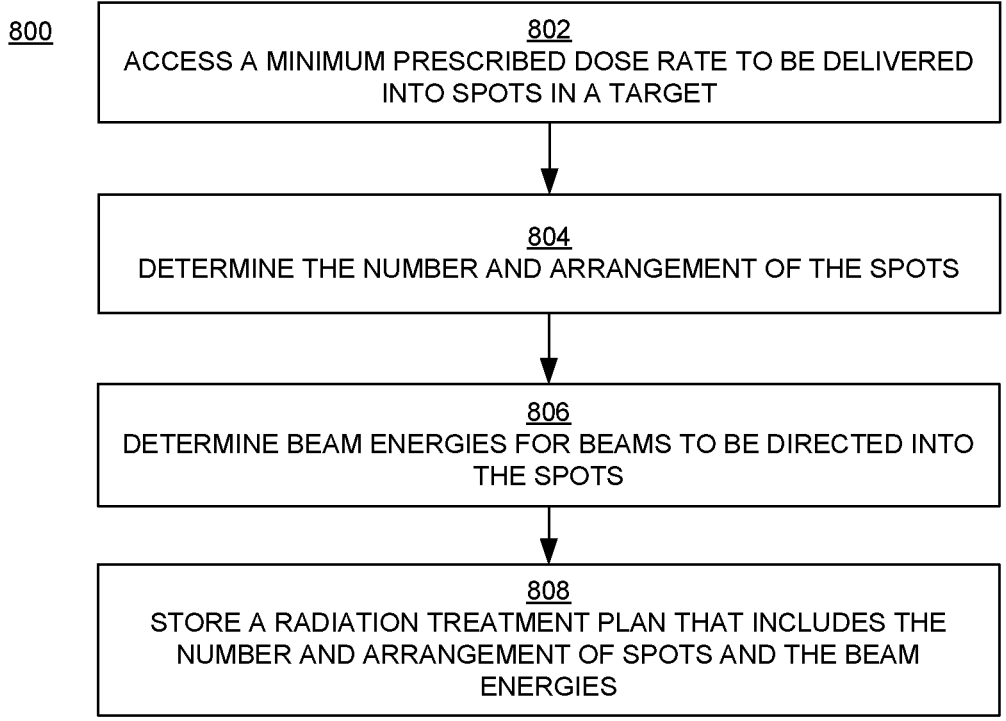
Figure 9:
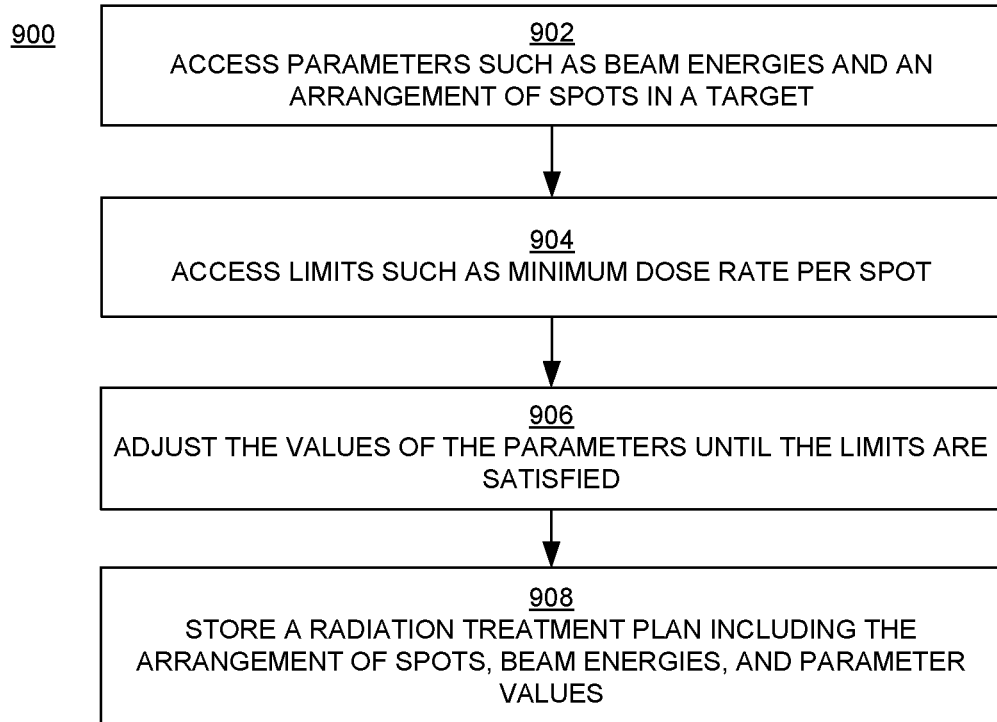

FIGS. 7, 8, and 9 are flowcharts 700, 800, and 900 of examples of computer-implemented operations for radiation treatment planning in embodiments according to the present invention. The flowcharts 700, 800, and 900 can be implemented as computer-executable instructions (e.g., the optimizer model 150 of FIG. 1) residing on some form of computer-readable storage medium (e.g., in memory of the computer system 100 of FIG. 1).

As mentioned above, in IMRT (e.g., IMPT), beam intensity is varied across each treatment region (target) in a patient, and in SFGRT, beams can be spatially and temporally fractionated. Depending on the treatment modality, the degrees of freedom available include beam shaping (collimation), beam weighting (spot scanning), beam intensity or energy, beam directions, dose rate, and number and arrangement of spots. Parameters that can affect dose rate also are considered. Such parameters include, but are not limited to, a number of irradiations of the target volume, a duration of each of the irradiations (irradiation times), and a dose deposited in each of the irradiations. The parameters may also include a period of time during which the irradiations are applied (e.g., a number of irradiations are applied over a period of time such as an hour, with each irradiation in the period of time separated from the next by another period of time) and an interval of time between each period of irradiations (e.g., each hour-long period is separated from the next by a day). If the target volume is divided into sub-volumes or voxels, then the values of the parameters can be on a per-sub-volume or per-voxel basis (e.g., a value per sub-volume or voxel). These degrees of freedom lead to an effectively infinite number of potential treatment plans, and therefore consistently and efficiently generating and evaluating high-quality treatment plans is beyond the capability of a human and relies on the use of a computing system, particularly considering the time constraints associated with the use of radiation therapy to treat ailments like cancer, as well as the large number of patients that are undergoing or need to undergo radiation therapy during any given time period.

The discussion to follow refers to beams, target volumes, doses, dose rates, and other elements or values. The discussion below is in the context of modeled elements and calculated values in the treatment planning tool set 310 and the optimizer model 150, unless otherwise noted or made clear in the discussion.

With reference to FIG. 7 and also to FIGS. 1, 4A, 4B, and 5, in block 702, information (e.g., data or an image) that includes a description of an outline of a target volume 408 inside a patient 410 to be treated with radiation is accessed from memory of the computer system 100.

In block 704, an arrangement of spots inside the outline of the target volume 408 is determined. Each the spots corresponds to a location inside the target volume 408 where a respective beam 412n or 423n of radiation is to be directed during radiation treatment of the patient.

In block 706, a dose rate for each beam 412n/423n of the beams 412/423 is determined. The dose rate per beam can be the same for all of the beams 412/423, or it can be different across some or all of the beams. That is, in general, each spot in the target does not necessarily have to receive the same dose and dose rate. The dose rate for each beam is a dose delivered in less than one second to a spot corresponding to that beam. For example, each beam can deliver at least 4 Gy in less than one second, and may deliver as much as 20 Gy to 50 Gy or 100 Gy or more in less than one second. In an embodiment, the ratio of the maximum dose rate or the maximum dose inside each spot, to the maximum dose rate or the maximum dose in areas outside the spots is at least 1.5. The areas outside the spots include the region 510 of FIG. 5, but can include areas outside that region; that is, the areas outside the spots in the target volume can be inside or outside the target 408.

In block 708, a radiation treatment plan, that includes the arrangement of the spots and the dose rate for each of the beams, is stored in computer system memory.

With reference now to FIG. 8, and continuing with reference to FIGS. 1, 4A, 4B, and 5, in block 802, a minimum prescribed dose rate to be delivered by either a sequence of the beams 412 or by the beams 423 into spots (e.g., the spots 504 and 506) in a target (e.g., the target volume 408) is accessed from memory of the computer system 100.

In block 804, a number of the spots and an arrangement of the spots in the target volume 408 is determined.

In block 806, a beam energy for each of the beams 412 or beams 423 is determined. The beam energy for each beam of the beams is determined such that each spot receives the minimum prescribed dose rate for that spot.

In block 808, a radiation treatment plan, that includes the number and arrangement of the spots and the beam energy for each of the beams, is stored in computer system memory.

With reference now to FIG. 9, and continuing with reference to FIGS. 1, 4A, 4B, and 5, in block 902, values of parameters are accessed from memory of the computer system 100. The parameters include the beam energies for the beams 412/423 to be directed into an arrangement of spots (e.g., the spots 504 and 506) in a target in a patient.

In block 904, information that specifies limits for the radiation treatment plan are accessed. The limits include a minimum limit on dose rate for each spot.

In block 906, the values of the parameters are adjusted until the dose rate for each spot satisfies the minimum limit on dose rate for that spot.

In block 908, a radiation treatment plan, that includes the arrangement of the spots, the beam energies for the beams, and the values of the parameters (from block 906), is stored in computer system memory.

Figure 10:
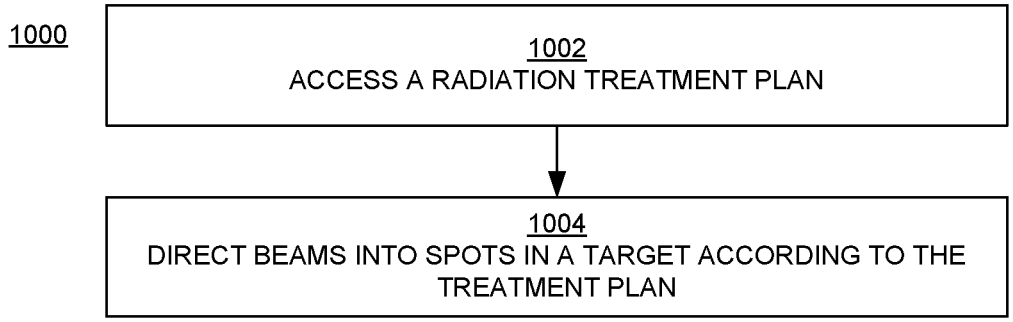
FIG. 10 is a flowchart of an example of a computer-implemented radiation treatment method in embodiments according to the present invention.

FIG. 10 is a flowchart 1000 of an example of a computer-implemented radiation treatment method in embodiments according to the present invention. The flowchart 1000 can be implemented as computer-executable instructions residing on some form of computer-readable storage medium (e.g., using the control system 410 of FIG. 4A or 4B).

In block 1002 of FIG. 10, with reference also to FIG. 1, a radiation treatment plan is accessed from memory of the computer system 100. In embodiments according to the invention, the radiation treatment plan is a plan that is generated according to, and includes the information determined according to, the methodologies discussed above, in particular the methodologies of FIGS. 7, 8, and 9.

In block 1004, beams are directed into spots in a target volume according to the treatment plan as described above in conjunction with FIGS. 4A, 4B, 5, and 6. In embodiments, after each of the spots in the target volume is treated with radiation as described above, a uniform dose rate is applied across the entire target volume (including the areas between the spots). The uniform dose rate may be at FLASH levels (e.g., at least 4 Gy in less than one second, and as much as 20 Gy to 50 Gy or 100 Gy or more in less than one second).

While the operations in FIGS. 7-10 are presented as occurring in series and in a certain order, the present invention is not so limited. The operations may be performed in a different order and/or in parallel, and they may also be performed in an iterative manner. As noted above, because of the different parameters that need to be considered, the range of values for those parameters, the interrelationship of those parameters, the need for treatment plans to be effective yet minimize risk to the patient, and the need to generate high-quality treatment plans quickly, the use of the optimizer model 150 executing consistently on the computer system 100 (FIG. 1) for radiation treatment planning as disclosed herein is important.

In summary, embodiments according to the invention improve radiation treatment planning and the treatment itself by expanding FLASH RT to a wider variety of treatment modalities and combinations of treatment modalities (e.g., SFGRT, in addition to IMRT and IMPT). Treatment plans generated as described herein are superior for sparing normal tissue from radiation in comparison to conventional techniques by reducing, if not minimizing, the magnitude (and the integral in some cases) of the dose to normal tissue (outside the target) by design. Combining the normal tissue sparing of FLASH RT with the tumor-killing effectiveness of SFGRT enables escalation of radiation dose in most tumors without the associated toxicities of conventional RT, and increase the number of indications treatable with FLASH dose rates. Treatment planning, while still a complex task of finding a balance between competing and related parameters, is simplified relative to conventional planning.

When used with FLASH dose rates, management of patient motion is simplified because the doses are applied in a short period of time (e.g., less than a second).

The techniques described herein may be useful for stereotactic radiosurgery as well as stereotactic body radiotherapy with single or multiple metastases.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer system, comprising:
   a processor; and
   memory coupled to the processor and comprising instructions that, when executed, cause the processor to execute operations to generate a radiation treatment plan, the operations comprising:
   accessing, from the memory, a minimum prescribed dose rate to be delivered by beams into spots in a target in a patient;
   determining a number of the spots and an arrangement of the spots in the target; and
   determining a beam energy for each beam of the beams, wherein the beam energy for said each beam of the beams is determined such that each spot of the spots receives the minimum prescribed dose rate.

2. The computer system of claim 1, wherein the minimum prescribed dose rate is four Grays per second.

3. The computer system of claim 1, wherein the minimum prescribed dose rate is 20 Grays per second.

4. The computer system of claim 1, wherein a ratio of dose rate inside a spot to a dose rate outside a spot is at least 1.5.

5. The computer system of claim 1, wherein the beams comprise a type of beam selected from the group consisting of: proton; electron; photon; atom nuclei; and ion.

6. The computer system of claim 1, wherein the beam energy for said each beam of the beams is determined using parameters comprising a number of irradiations for a respective spot corresponding to said each beam, a duration of each irradiation of the irradiations for the respective spot, and a dose deposited in each irradiation of the irradiations for the respective spot.

7. The computer system of claim 6, wherein the parameters further comprise: a period of time during which the irradiations are applied, and an interval of time between each period of irradiations.

8. The computer system of claim 1, wherein the operations further comprise determining a dose rate for said each beam of the beams.

9. The computer system of claim 8, wherein the dose rate for said each beam is a dose delivered in less than one second to a respective spot corresponding to said each beam.

10. The computer system of claim 1, wherein the operations further comprise storing, to the memory, the radiation treatment plan, wherein the radiation treatment plan comprises the arrangement of the spots and the beam energy for said each beam of the beams.

11. A computer-implemented method of radiation treatment planning, the method comprising:
    accessing, from memory of a computer system, a minimum prescribed dose rate to be delivered by beams into spots in a target in a patient;
    determining a number of the spots and an arrangement of the spots in the target; and
    determining a beam energy for each beam of the beams, wherein the beam energy for said each beam of the beams is determined such that each spot of the spots receives the minimum prescribed dose rate.

12. The method of claim 11, wherein the minimum prescribed dose rate is four Grays per second.

13. The method of claim 11, wherein the minimum prescribed dose rate is 20 Grays per second.

14. The method of claim 11, wherein a ratio of dose rate inside a spot to a dose rate outside a spot is at least 1.5.

15. The method of claim 11, wherein the beams comprise a type of beam selected from the group consisting of: proton; electron; photon; atom nuclei; and ion.

16. The method of claim 11, wherein the beam energy for said each beam of the beams is determined using parameters comprising a number of irradiations for a respective spot corresponding to said each beam, a duration of each irradiation of the irradiations for the respective spot, and a dose deposited in each irradiation of the irradiations for the respective spot.

17. The method of claim 16, wherein the parameters further comprise: a period of time during which the irradiations are applied, and an interval of time between each period of irradiations.

18. The method of claim 11, further comprising determining a dose rate for said each beam of the beams.

19. The method of claim 18, wherein the dose rate for said each beam is a dose delivered in less than one second to a respective spot corresponding to said each beam.

20. The method of claim 11, further comprising storing, to memory of a computer system, a radiation treatment plan comprising the arrangement of the spots and the beam energy for said each beam of the beams.

* * * * *